United States Patent
Noshi

(10) Patent No.: US 9,316,745 B2
(45) Date of Patent: Apr. 19, 2016

(54) X-RAY CT APPARATUS AND METHOD OF CONTROLLING THE SAME

(71) Applicants: Kabushiki Kaisha Toshiba, Minato-Ku (JP); Toshiba Medical Systems Corporation, Otawara-Shi (JP)

(72) Inventor: Yasuhiro Noshi, Otawara (JP)

(73) Assignees: KABUSHIKI KAISHA TOSHIBA, Minato-ku (JP); TOSHIBA MEDICAL SYSTEMS CORPORATION, Otawara-shi (JP)

(*) Notice: Subject to any disclaimer, the term of this patent is extended or adjusted under 35 U.S.C. 154(b) by 15 days.

(21) Appl. No.: 13/939,573

(22) Filed: Jul. 11, 2013

(65) Prior Publication Data

US 2014/0023181 A1 Jan. 23, 2014

(30) Foreign Application Priority Data

Jul. 17, 2012 (JP) .................................. 2012-159068

(51) Int. Cl.
- A61B 6/00 (2006.01)
- A61B 6/03 (2006.01)
- G01T 1/17 (2006.01)
- A61B 6/12 (2006.01)

(52) U.S. Cl.
CPC ............... *G01T 1/17* (2013.01); *A61B 6/4241* (2013.01); *A61B 6/467* (2013.01); *A61B 6/482* (2013.01); *A61B 6/032* (2013.01); *A61B 6/12* (2013.01); *A61B 6/463* (2013.01); *A61B 6/469* (2013.01); *A61B 6/542* (2013.01); *A61B 6/56* (2013.01)

(58) Field of Classification Search
CPC .............................. A61B 6/4241; A61B 6/482
USPC ........................................................ 378/19, 4
See application file for complete search history.

(56) References Cited

U.S. PATENT DOCUMENTS

| | | |
|---|---|---|
| 2007/0076842 A1 | 4/2007 | Tkaczyk et al. |
| 2007/0237288 A1 | 10/2007 | Tkaczyk et al. |
| 2010/0135565 A1 | 6/2010 | Thomsen et al. |
| 2010/0310036 A1 | 12/2010 | Burleton et al. |
| 2011/0243413 A1 | 10/2011 | Tkaczyk et al. |
| 2013/0108013 A1 | 5/2013 | Leng et al. |

FOREIGN PATENT DOCUMENTS

| | | |
|---|---|---|
| DE | 10 2007 027 460 A1 | 12/2008 |
| JP | 2006-101926 | 4/2006 |

(Continued)

OTHER PUBLICATIONS

Extended European Search Report issued Nov. 22, 2013 in Patent Application No. 13176553.9.

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

According to one embodiment, an X-ray CT apparatus includes an energy classifying unit, a setting unit, and an image generating unit. The energy classifying unit is configured to classify photons passing through an object into a number of energy bins in accordance with energy of the photons. The setting unit is configured to set an energy level and set an energy width of a plurality of energy bins of the number of energy bins. The image generating unit is configured to generate an extended energy bin image based on information on the photons classified into the plurality of energy bins, the image having the energy level and the energy width of the plurality of energy bins.

19 Claims, 7 Drawing Sheets

(56) References Cited

FOREIGN PATENT DOCUMENTS

| WO | WO 2012/009725 A1 | 1/2012 |
| WO | WO2012009725 * | 1/2012 |
| WO | WO 2012/088243 A2 | 6/2012 |

* cited by examiner

X-RAY CT APPARATUS AND METHOD OF CONTROLLING THE SAME

CROSS-REFERENCE TO RELATED APPLICATIONS

This application claims the benefit of priority of Japanese Patent Application No. 2012-159068, filed July 17, 2012, the entire contents of which are incorporated herein by reference.

FIELD

Embodiments described herein relate generally to an X-ray CT (Computed Tomography) apparatus and a method of controlling the X-ray CT apparatus.

BACKGROUND

Some X-ray CT apparatuses using photon counting to detect photons of X-rays classify the photons received by a detector into respective energy bins. Such an X-ray CT apparatus using photon counting can generate an image for each energy bin.

Unfortunately, the count of photons in each energy bin may be insufficient for the generation of an image having less noise. In such a case, some or all of the images generated for the respective energy bins are noisy.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray CT apparatus and a method of controlling the X-ray CT apparatus according to embodiments of the present invention with reference to the drawings.

In general, according to one embodiment, an X-ray CT apparatus includes an energy classifying unit, a setting unit, and an image generating unit. The energy classifying unit is configured to classify photons passing through an object into a number of energy bins in accordance with energy of the photons. The setting unit is configured to set an energy level and set an energy width of a plurality of energy bins of the number of energy bins. The image generating unit is configured to generate an extended energy bin image based on information on the photons classified into the plurality of energy bins, the image having the energy level and the energy width of the plurality of energy bins.

There are various types of X-ray CT apparatuses of the present embodiment, such as a ROTATE/ROTATE type in which an X-ray tube and an X-ray detector rotate as one body around an object, a STATIONARY/ROTATE type in which a large number of detection elements are arrayed in a ring-shape, and only the X-ray tube rotates around the object, and the like. The present invention can be applied to any of those types. Hereafter, the ROTATE/ROTATE type which is currently in a mainstream position will be described.

Further, the current mainstream of the mechanism for converting incoming X-ray into electric charge includes an indirect conversion type in which X-ray is converted into light with a fluorescent body such as a scintillator, etc., and the light is converted into electric charge with a photoelectric conversion element such as a photodiode, etc., and a direct conversion type in which the generation of an electron-hole pair in a semiconductor and the transfer thereof to an electrode, that is, a photoconductive phenomenon is utilized.

In addition, in recent years, a progress has been made in the commercialization of a so-called multi-tube type X-ray CT apparatus, in which a plurality of pairs of the X-ray tube and the X-ray detector are mounted on a rotary ring, and the development of peripheral technologies thereof has been in progress. The X-ray CT apparatus of the present embodiment can be applied to either of a conventional single-tube type X-ray CT apparatus, or a multi-tube type X-ray CT apparatus. Here, description will be made supposing a single-tube type X-ray CT apparatus.

Figure 1:
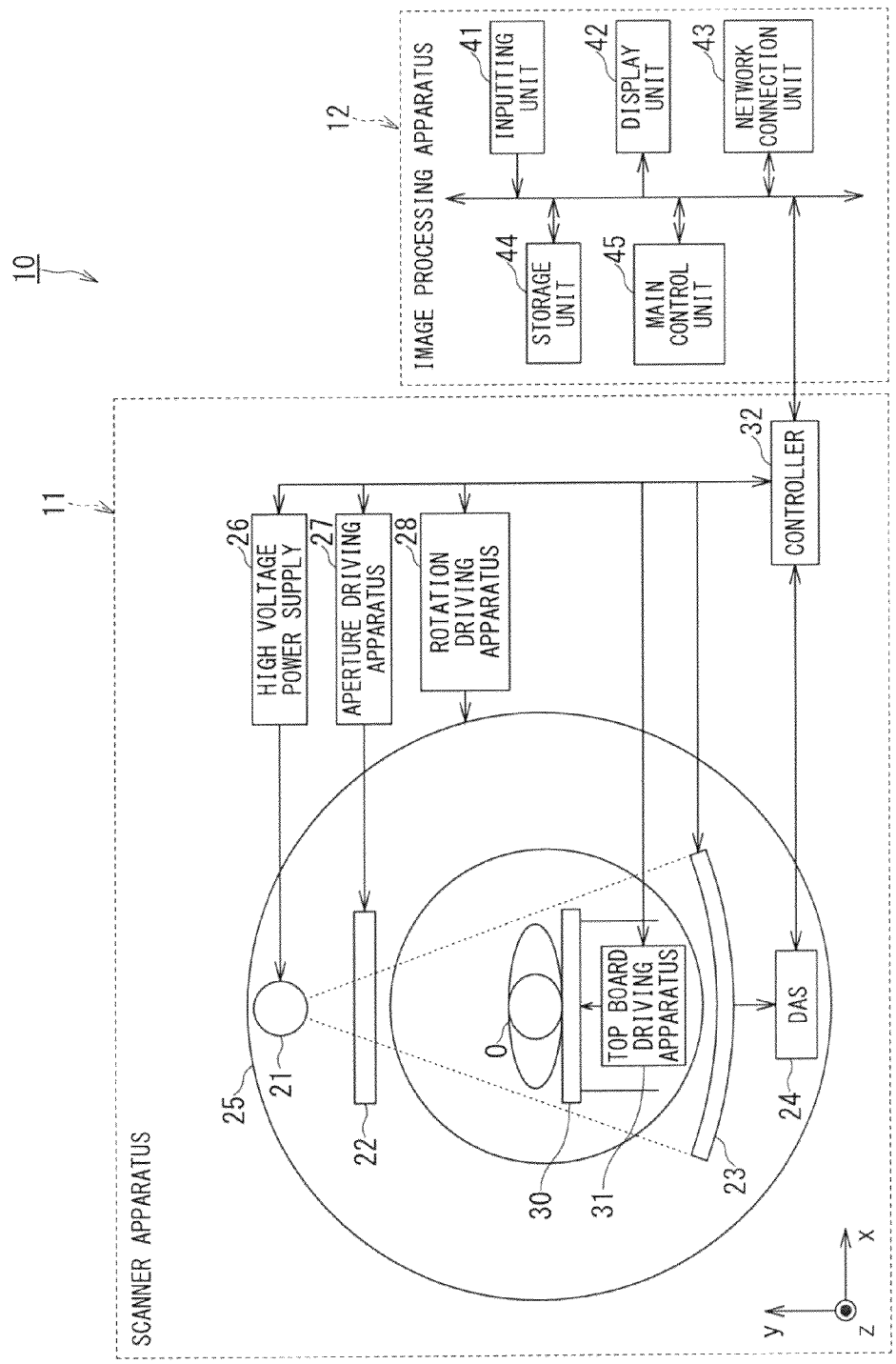
FIG. 1 is a schematic block diagram illustrating an entire configuration of an exemplary X-ray CT apparatus using photon counting, according to an embodiment of the present invention.

FIG. 1 is a schematic block diagram illustrating an entire configuration of an exemplary X-ray CT apparatus 10 using photon counting, according to an embodiment of the present invention.

The X-ray CT apparatus using photon counting 10, as illustrated in FIG. 1, includes a scanner apparatus 11 and an image processing apparatus 12. The scanner apparatus 11 of the X-ray CT apparatus 10 is usually installed in an examination room and generates X-ray transmission data associated with individual parts of a patient O (object). The image processing apparatus 12 is usually installed in a control room adjacent to the examination room and generates projection data according to the transmission data to generate and display a reconstruction image.

The scanner apparatus 11 of the X-ray CT apparatus 10 includes an X-ray tube 21, an aperture 22, an X-ray detector using photon counting (hereinafter, simply referred to as "X-ray detector") 23, a DAS (Data Acquisition System) 24, a rotation unit 25, a high voltage power supply 26, an aperture driving apparatus 27, a rotation driving apparatus 28, a top board 30, a top board driving apparatus 31, and a controller 32.

The X-ray tube 21 generates X-rays in response to the application of voltage (hereinafter, referred to as "tube voltage") by the high voltage power supply 26. The X-rays generated from the X-ray tube 21, which are fan beam X-rays or cone beam X-rays, are emitted to the patient O.

The aperture 22 is controlled by the controller 32 through the aperture driving apparatus 27 to adjust a range of the irradiation with the X-rays from the X-ray tube 21 in a slice direction.

The X-ray detector 23 includes one or more X-ray detecting elements (electrical charge accumulating elements). The X-ray detecting elements detect the X-rays emitted from the X-ray tube 21. The X-ray tube 21 and the X-ray detector 23 are supported in the rotation unit 25 so as to face each other across the patient O placed on the top board 30.

The X-ray detector 23 may be of a multi-slice type, or a two-dimensional array type, in which rows of X-ray detecting elements each having multiple channels along the channel (X axis) direction are arranged in the slice (Z axis) direction. The two-dimensional array type detector may include multiple X-ray detecting elements distributed in a dense arrangement in both the channel (X axis) and slice (Z axis) directions.

The DAS 24 amplifies the signals of the transmission data detected by X-ray detecting elements constituting the X-ray detector 23, converts the signals into digital ones, and outputs the digital signals. The data output from the DAS 24 is sent to the image processing apparatus 12 through the controller 32 of the scanner apparatus 11.

The rotation unit 25 integrally holds the X-ray tube 21, the aperture 22, the X-ray detector 23, and the DAS 24. The rotation unit 25 is controlled by the controller 32 to rotate through the rotation driving apparatus 28, leading to the integral rotation of the X-ray tube 21, the aperture 22, the X-ray detector 23, and the DAS 24 about the patient 0.

The high voltage power supply 26 is controlled by the controller 32 to supply the X-ray tube 21 with power needed for the irradiation with X-rays. The image processing apparatus 12 provides the controller 32 with information on a timing and duration of the generation of the X-rays from the X-ray tube 21 and information on the values of tube current and tube voltage to be applied to the X-ray tube 21.

The aperture driving apparatus 27 is controlled by the controller 32 to adjust an opening of the aperture 22, leading to the adjustment of a range for the irradiation with the X-rays along the slice direction.

The rotation driving apparatus 28 is controlled by the controller 32 to rotate the rotation unit 25 around a cavity portion.

The top board 30 is configured so that the patient O can be placed on the board. The top board driving apparatus 31 is controlled by the controller 32 to lift and lower the top board 30 in the Y axis direction. The top board driving apparatus 31 is also controlled by the controller 32 to move the top board 30 along the Z axis direction to an X-ray irradiation field of an opening portion at the center of the rotation unit 25.

The controller 32 includes a central processing unit (CPU) and storage media, such as random access memory (RAM) and read-only memory (ROM). The controller 32 controls the X-ray detector 23, the DAS 24, the high voltage power supply 26, the aperture driving apparatus 27, the rotation driving apparatus 28, and the top board driving apparatus 31 to carry out a scan in accordance with programs stored in the storage media. The RAM in the controller 32 provides a work area for temporary storage of data and a program being executed by the CPU. The storage media such as the ROM of the controller 32 store programs for starting and controlling the scanner apparatus 11 and various items of data required to execute these programs.

Note that the storage media such as the ROM of the controller 32 may include a CPU readable recording medium such as a magnetic or an optical recording medium or semiconductor memory, and some or all of the programs and data in the storage media may be downloaded via an electronic network.

On the other hand, the image processing apparatus 12 of the X-ray CT apparatus using photon counting 10 may be, for example, a personal computer, which can send and receive data through a network such as a backbone LAN (local area network) in a hospital.

The image processing apparatus 12, as illustrated in FIG. 1, includes an inputting unit 41, a display unit 42, a network connection unit 43, a storage unit 44, and a main control unit 45.

The inputting unit 41 is a common input device such as a keyboard, a trackball, a touch-sensitive panel, and a numeric keypad, and outputs operational input signals corresponding to user operations to the main control unit 45. For example, when a user sets up a scan plan through the inputting unit 41, the main control unit 45 instructs the controller 32 of, for example, the timing and duration of irradiation and of the values of tube current and tube voltage to be applied to the X-ray tube 21, according to the scan plan. The controller 32 then causes the high voltage power supply 26 to supply the X-ray tube 21 with power in compliance with the information from the main control unit 45, such as the timing and duration of the irradiation, the tube current, and the tube voltage.

The display unit 42 is, for example, a common display device such as a liquid crystal display and an OLED (organic light emitting diode) display and displays a variety of images such as images of their respective energy bins in accordance with the control by the main control unit 45.

The network connection unit 43 can use a variety of information communications protocols in accordance with the individual types of networks. The network connection unit 43 connects the image processing apparatus 12 to other electrical equipment such as an image server, in compliance with the protocols. The connection may be electrically provided through an electronic network.

The electronic network, as used herein, refers to the general communications network utilizing the telecommunications technology. Examples of the electronic network include a wireless/wired LAN such as a backbone LAN in a hospital, the Internet, a telephone communication network, a fiber optic communication network, a cable communication network, and a satellite communication network.

The storage unit 44 includes a recording medium, such as a magnetic or optical recording medium or semiconductor memory, which is readable and writable by a CPU in the main control unit 45, and some or all of the programs and data in the storage medium may be downloaded via an electronic network. The storage unit 44, for example, stores data collected by the scanner apparatus 11, information on a relation between a lesion and an energy width, and information on a relation between a region and an energy width.

The main control unit 45 includes the CPU and storage media such as RAM and ROM. The main control unit 45 controls the controller 32 in the scanner apparatus 11 on the basis of scanner controlling programs stored in the storage media.

The CPU of the main control unit 45 loads an energy level/energy width (EL/EW) modifying program and data required for the execution of the program, which are stored in the storage media such as the ROM, into the RAM. The CPU then modifies the width of the energy bins on the basis of the program in response to a user input operation, while executing a process for generating an image according the modification in real time.

The RAM of the main control unit 45 provides a work area for temporary storage of data and a program being executed by the CPU. The storage media such as the ROM of the main control unit 45 store an EL/EW modifying program and various items of data required to execute the program.

Note that the storage media, such as the ROM, include a CPU readable recording medium such as a magnetic or an optical recording medium or semiconductor memory, and some or all of the programs and data in the storage media may be downloaded via an electronic network.

Figure 2:
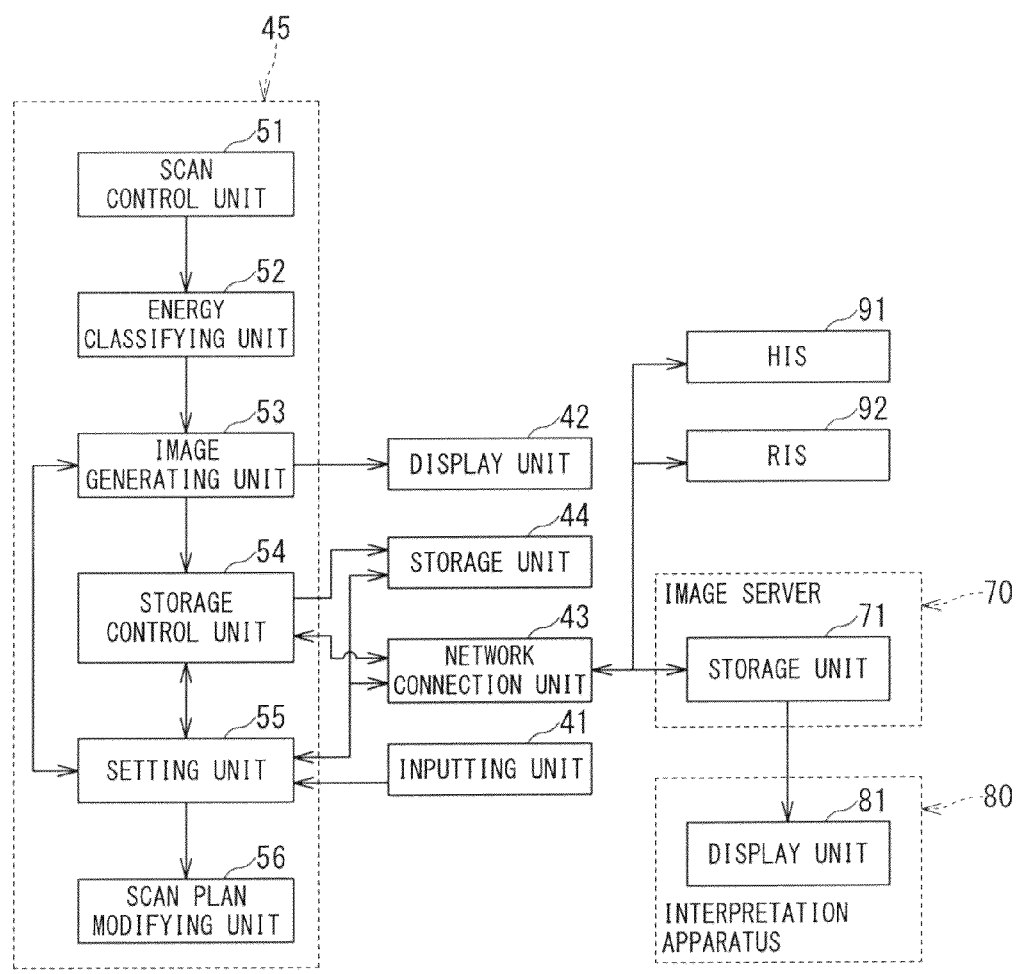
FIG. 2 is a schematic block diagram illustrating an exemplary configuration of units that realize functions by the CPU of the main control unit.

FIG. 2 is a schematic block diagram illustrating an exemplary configuration of units that realize functions by the CPU of the main control unit 45. Note that these units may also be configured by hardware logic such as a circuit, without any CPU.

The CPU of the main control unit 45, as illustrated in FIG. 2, uses the EL/EW modifying program to function as at least a scan control unit 51, an energy classifying unit 52, an image generating unit 53, a storage control unit 54, a setting unit 55, and a scan plan modifying unit 56. The each of the units 51 to 56 uses a required work area of the RAM as a temporary storage area for data.

In response to an input of an instruction to carry out a scan plan from a user through the inputting unit 41, the scan control unit 51 controls the scanner apparatus 11 through the controller 32 to perform a scan according to the scan plan. As a result, information on photons passing through the object O is sent to the energy classifying unit 52 from the scanner apparatus 11.

The energy classifying unit 52 controls the DAS 24 through the controller 32 to classify the photons passing through the object O into a certain predetermined number of individual energy bins in accordance with the energy of the photons.

Figure 3:
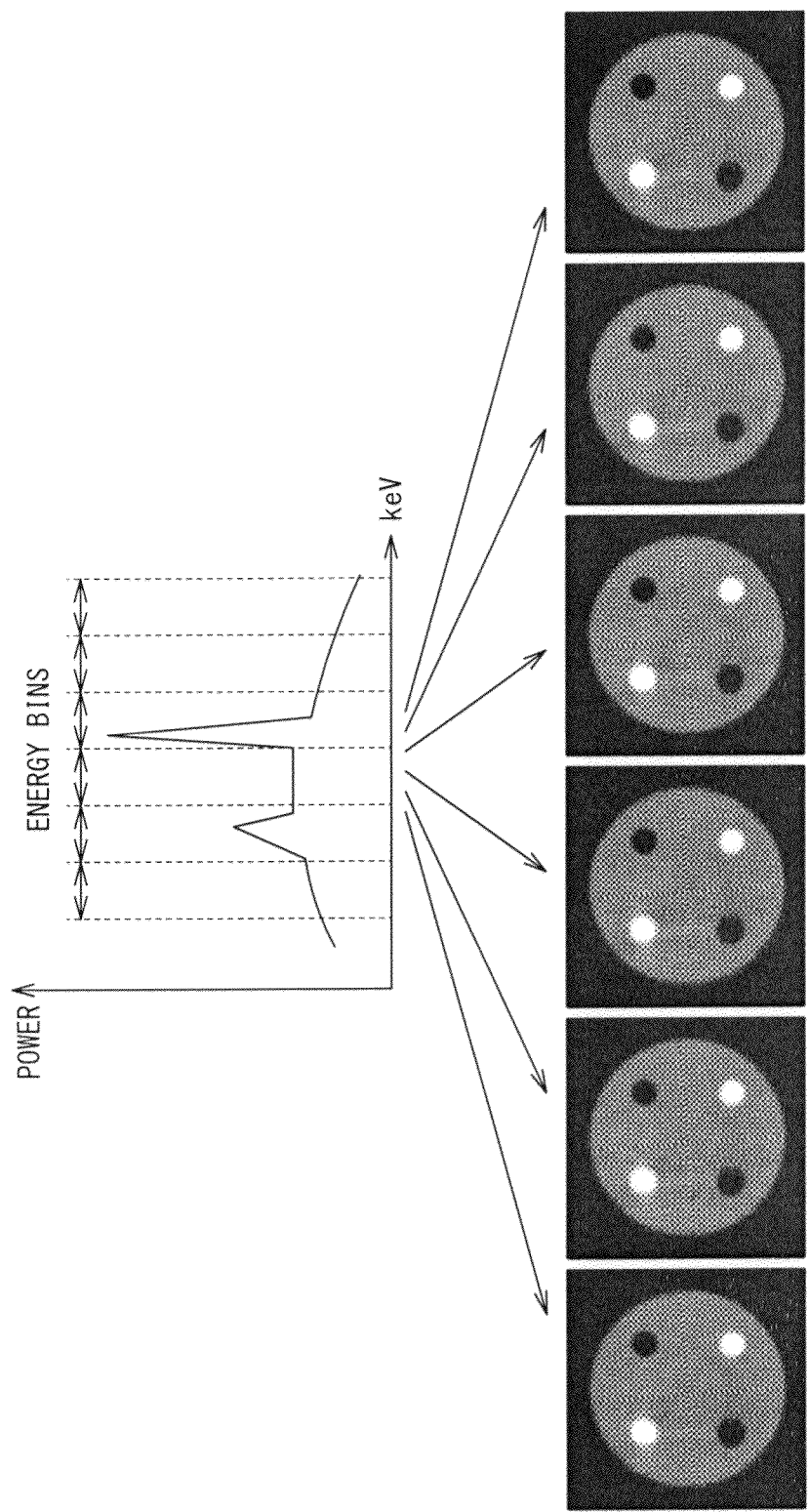
FIG. 3 is an explanatory drawing illustrating an example of energy bins and an example of energy bin images which corresponding to the respective energy bins.

FIG. 3 shows an example of energy bins and an example of energy bin images which corresponding to the respective energy bins. Note that the example energy bin images shown in FIG. 3 are generated by using an object O that is a phantom including water and four rods made of different materials (e.g., rods of air, nylon, and carbon fluoride resin) in the water.

Any energy bin including an insufficient number of photons would cause the noise level of the corresponding energy bin image in FIG. 3 to be high. As a result, an image displayed as an initial image may have low user visibility.

To address this, on the basis of information on the photons of the multiple energy bins, the X-ray CT apparatus using photon counting 10 according to the present embodiment generates an extended energy bin image having an energy level EL set by the setting unit 55 and an energy width EW of some of the predetermined number of energy bins. As a result, because of an increased number of photons, the extended energy bin image may have a lower noise level than that of each energy bin image generated based on information on photons assigned to a single energy bin.

The image generating unit 53, on the basis of the information on the photons classified into the multiple energy bins, generates such an extended energy bin image having the energy level EL and the energy width EW of some of the predetermined number of energy bins, the EL and EW being set by the setting unit 55. The image generating unit 53 allows the display unit 42 to display the extended energy bin generated image.

The setting unit 55 sets the energy level EL and the energy width EW in accordance with various types of information.

For example, the setting unit 55 may be configured to acquire information on a lesion associated with the object O to set an energy width EW on the basis of information on a relation between the lesion and the energy width depending on the information on the lesion. In such a case, the optimum energy width EW according to the lesion may be readily set.

Such information on a relation between a lesion and an energy width EW may be preliminarily stored in the storage unit 44 or may be acquired via a network. The information on a lesion associated with the object O may be included, for example, in a scan plan; otherwise, such information may be acquired from a hospital information system (HIS) server 91 or a radiology information system (RIS) server 92 connected to the network via the network connection unit 43.

The setting unit 55 may be configured to set the energy level EL depending on the lesion information, in response to an instruction from the user through the inputting unit 41, or depending on the predetermined initial value. In the case of setting the energy level EL depending on the lesion information, the information on the relation between the lesion and the energy level EL may be preliminarily stored in the storage unit 44 or may be acquired via a network.

The setting unit 55 may also be configured to acquire information on a region of interest to set an energy width EW on the basis of information on a relation between the region and an energy width depending on the information on the region of interest. This can facilitate the setting of the optimum energy width EW depending on the region.

Such information on a relation between a region of interest and an energy width may be preliminarily stored in the storage unit 44 or may be acquired via a network. The information on a region of interest may be included, for example, in a scan plan; otherwise, such information may be acquired from the HIS server 91 and the RIS server 92 connected to the network via the network connection unit 43.

The setting unit 55 may be configured to set the energy level EL depending on the region information, in response to an instruction from the user through the inputting unit 41, or depending on the predetermined initial value. In the case of setting the energy level EL depending on the region information, the information on the relation between the region and the energy level EL may be preliminarily stored in the storage unit 44 or may be acquired via a network.

The setting unit 55 may be configured to further acquire information on a lesion and information on a region to set an energy width EW on the basis of information on a relation between the lesion information, the region information, and the energy width depending on the lesion information and the region information both. For example, if the lesion is "cancer" and the region is "liver," the setting unit 55 may be configured to set an energy width EW appropriate for "liver cancer." In this case, the information on the relation between the lesion information, the region information, and the energy width may be preliminarily stored in the storage unit 44 or may be acquired via a network.

Also in this case, the setting unit 55 may be configured to set the energy level EL depending on the lesion information and the region information both, in response to an instruction from the user through the inputting unit 41, or depending on the predetermined initial value. In the case of setting the energy level EL depending on the lesion information and the region information both, the information on the relation between the lesion, the region, and the energy level EL may be preliminarily stored in the storage unit 44 or may be acquired via a network.

The setting unit 55 may also be configured to acquire instruction information about an energy level EL and an energy width EW via the inputting unit 41 to set the energy width EW depending on the instruction information.

The setting unit 55 may also be configured to set an energy level EL and an energy width EW using initial values of the energy level EL and the energy width EW of multiple energy bins preliminarily determined and stored in the storage unit 44.

The setting unit 55 may also be configured to acquire information on an X-ray exposure dose included in a scan plan to set an energy width EW depending on the information on the X-ray exposure dose. Since noise in an energy bin image should increase with lowering X-ray exposure dose, an energy width EW is preferably set with reference to the information on the X-ray exposure dose so as to reduce noise in an extended energy bin image.

The setting unit 55 may be configured to set the energy level EL depending on the region information, in response to an instruction from the user through the inputting unit 41, or depending on the predetermined initial value. In the case of setting the energy level EL depending on the region information, the information on the relation between the region and the energy level EL may be preliminarily stored in the storage unit 44 or may be acquired via a network.

Furthermore, the setting unit 55 may be configured to set an energy width EW based on the lesion information, the region information, the user input, the initial value, or the like, and then adjust and reset the set energy width EW on the basis of the information on the X-ray exposure dose included in the scan plan.

The image generating unit 53 may also be configured to generate energy bin images respectively corresponding to a predetermined number of energy bins (see FIG. 3) and control the storage control unit 54 to store the generated images in the storage unit 44. Each of the energy bins has a predetermined energy width EW around its energy level EL. At this time, the image generating unit 53 may be configured to display one of the predetermined number of generated energy bin images on the display unit 42 as an initial image.

If an energy level EL and an energy width EW are preset in the scan plan, the image generating unit 53 generates and display an initial image having the energy level EL and the energy width EW on the display unit 42; otherwise, the image generating unit 53 displays an energy bin image of a predetermined energy bin on the display unit 42 as an initial image (a representative image of a predetermined number of energy bin images). Furthermore, an extended energy bin image may also be displayed together with an initial image.

After the display of the initial image, the image generating unit 53 may be configured to generate an extended energy bin image having an energy level EL and an energy width EW modified according to an instruction received through the inputting unit 41 from the user, who confirms the initial image.

Figure 4:
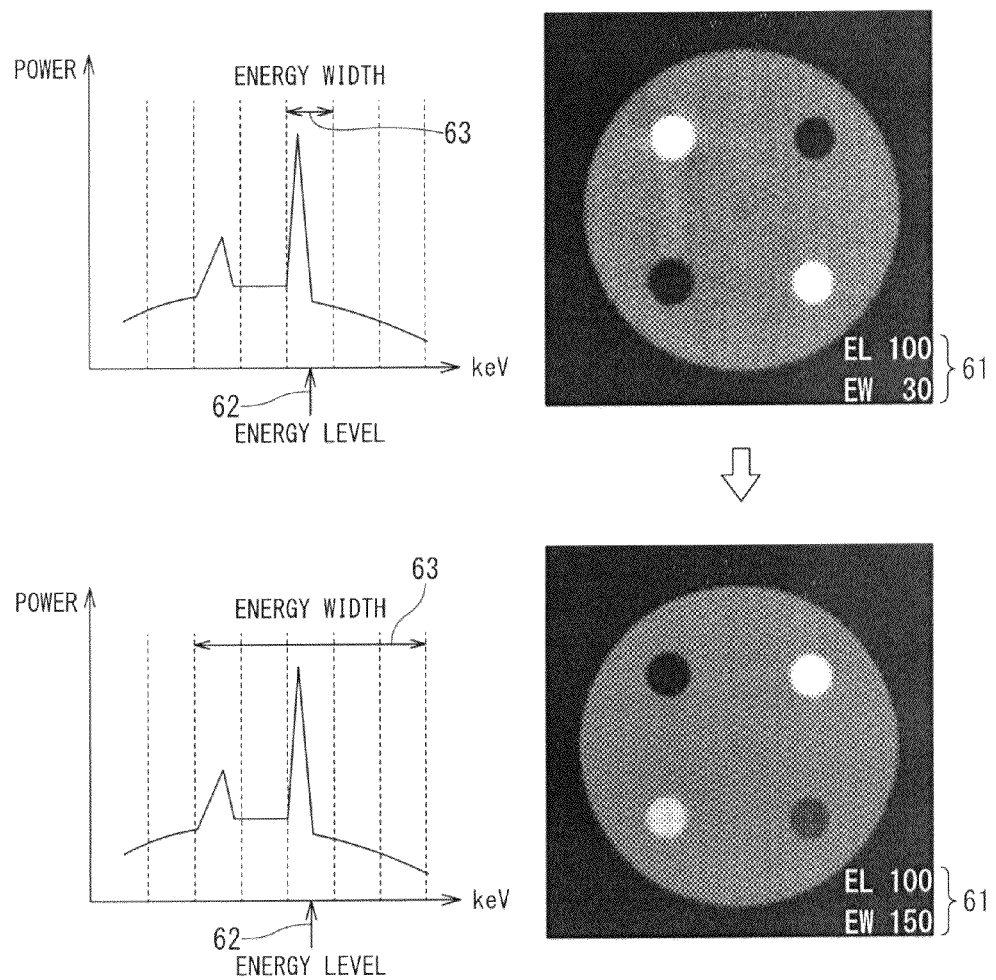
FIG. 4 is an explanatory drawing illustrating an example of a relationship between an initial image and an extended energy bin image, the extended energy bin image having an energy level EL and an energy width EW obtained by modifying those of the initial image according to an input operation by a user.
Figure 5A:
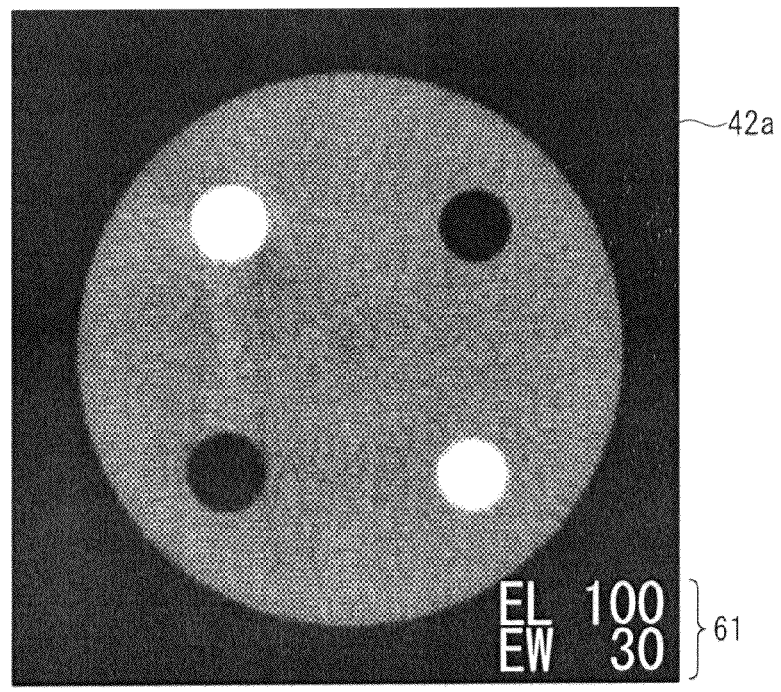
FIG. 5A is an explanatory drawing illustrating an example of a display screen of the display unit displaying the initial image in FIG. 4.

FIG. 4 shows an example of a relationship between an initial image and an extended energy bin image having an energy level EL and an energy width EW obtained by modifying those of the initial image according to an input operation by a user. FIG. 5A shows an example of a display screen 42a of the display unit 42 displaying the initial image in FIG. 4, while FIG. 5B shows an example of the display screen 42a of the display unit 42 displaying the extended energy bin image in FIG. 4.

Although FIGS. 4 and 5 show an example of the initial image and the extended energy bin image having the same energy level EL, the initial image and the extended energy bin image may also have each different energy level EL. FIGS. 4 and 5 show an example energy width EW of each energy bin, i.e., 30 keV. Also, FIGS. 4 and 5 show an example of the display unit 42 displaying the energy bin image of the energy bin having an energy level of 100 keV, the image being preliminarily defined as an initial image.

The images shown in the upper right of FIG. 4 and in FIG. 5A are example initial images. In addition, an energy distribution represented by the counts of photons is shown in the upper left of FIG. 4, the distribution including examples of an image 62 indicating the position of the energy level EL of the initial image and an image 63 indicating the energy width EW of the initial image.

Figure 5B:
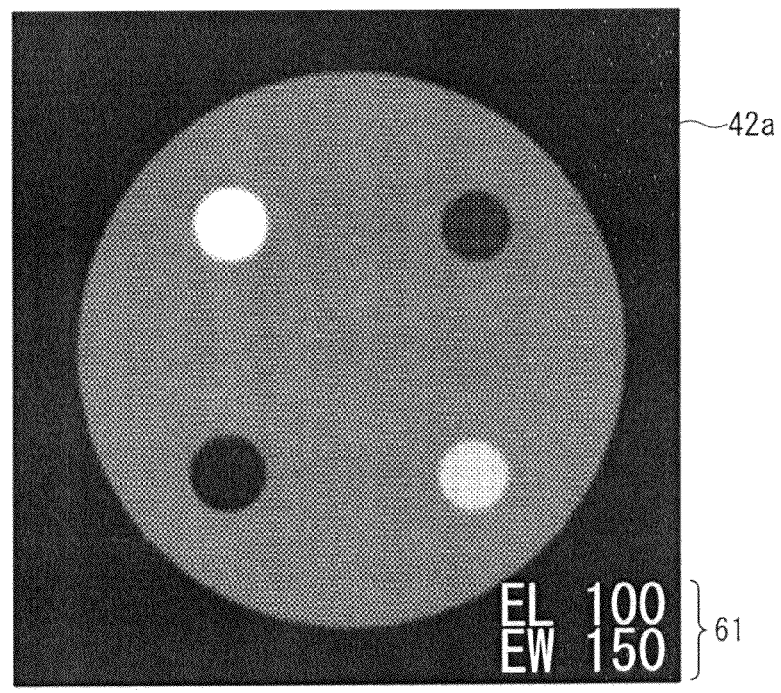
FIG. 5B is an explanatory drawing illustrating an example of the display screen of the display unit displaying the extended energy bin image in FIG. 4.

Furthermore, the images shown in the lower right of FIG. 4 and in FIG. 5B are example extended energy bin images. In addition, an energy distribution represented by the counts of photons is shown in the lower left of FIG. 4, the distribution including examples of the image 62 indicating the position of the energy level EL of the extended energy bin image and the image 63 indicating the energy width EW of the extended energy bin image. The image generating unit 53 superimposes an image (e.g., a character information image) 61 indicating the corresponding energy level EL and energy width EW on each of the initial image and the extended energy bin image.

For example, in the case of the inputting unit 41 provided with a trackball for determining the energy level EL and a trackball for determining the energy width EW, the user can operate these trackballs to readily determine the energy level EL and the energy width EW of the extended energy bin image.

The image generating unit 53 acquires an instruction input by the user from the setting unit 55 each time and generates an extended energy bin image in real time according to the instruction by the user. Thus, the user can modify the energy level EL and the energy width EW through the inputting unit 41 and confirm an extended energy bin image altered in real time according to the modification, thereby readily confirming the energy level EL and the energy width EW for achieving a desired image.

The extended energy bin image is generated on the basis of information on photons classified into multiple energy bins associated with the set energy level EL and energy width EW. Specifically, for example, the extended energy bin image can be generated by averaging multiple energy bin images that are generated during the generation of an initial image. For example, in the case of the energy width EW of each energy bin being 30 keV, if the setting unit 55 sets an energy width at 150 keV, the image generating unit 53 generates an extended energy bin image by averaging five energy bin images around the energy level EL set by the setting unit 55 (see the lower stage in FIG. 4). Alternatively, the image generating unit 53 may be configured to generate an extended energy bin image using a weighted average. The weighting may emphasize the image of the energy level EL associated with the energy bin set by the setting unit 55, for example.

Figure 6:
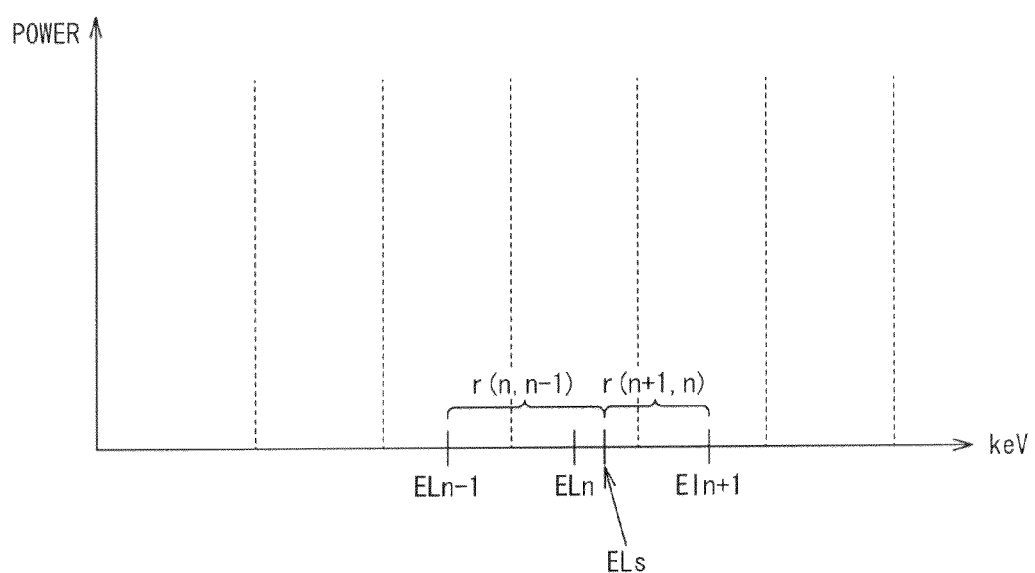
FIG. 6 is a drawing illustrating an example method of generating an extended energy bin image in the case where a set energy level ELs is not the middle energy of the energy bin.

FIG. 6 illustrates an example method of generating an extended energy bin image in the case where a set energy level ELs is not the middle energy of the energy bin.

For example, assume that the energy level ELs set by an instruction from the user is not the middle energy of the energy bin. In this case, for example, energy differences r(n+1, n), r(n, n−1), r(n+2, n), r(n, n−2), etc. between the determined energy level ELs and each of the middle energies of surrounding energy bins $EL_{n+1}, EL_{n-1}, EL_{n+2}, EL_{n-2}$, etc. are defined. Then, the average of the energy bin images may be obtained after the assignment of weights to the individual energy bin images depending on the energy differences.

The image generating unit 53, as shown in FIG. 4, may be further configured to further display the energy distribution image represented by the counts of photons with the extended energy bin image. The image generating unit 53 may superimpose the image 62 indicating information on the corresponding energy level EL and the image 63 indicating information on the corresponding energy width EW on the energy distribution image (see FIG. 4). In this case, when the user modifies the energy level EL and the energy width EW, the image generating unit 53 alters the extended energy bin image in real time and also modify the image 62 indicating information on the energy level EL and the image 63 indicating information on the energy width EW (e.g., in an example shown in FIG. 4, adjusting the length of the arrow, which is the image 63).

The storage control unit 54 controls the storage unit 44 to store a predetermined number of energy bin images generated by the image generating unit 53. The storage control unit 54 is also configured to control the storage unit 44 to store an extended energy bin image generated by the image generating unit 53 and determined by a user, in association with additional information being the energy level EL and energy width EW corresponding to the extended energy bin image. The storage control unit 54 is also configured to control a storage unit 71 of an image server 70 network-connected via the network connection unit 43 to store the extended energy bin image in association with additional information. As a result, an operator of a interpretation apparatus 80 network-connected to the image server 70 can confirm the extended energy bin image and the additional information for the extended energy bin image through a display unit 81 of the interpretation apparatus 80.

The setting unit 55, as described above, sets an energy level EL and an energy width EW according to various types of information and provide the image generating unit 53 with the set data. The setting unit 55 is also configured to receive an instruction to determine the extended energy bin image from the user through the inputting unit 41 and provide the storage control unit 54 and the scan plan modifying unit 56 with information on the reception of the instruction.

When receiving the instruction from the user to determine the extended energy bin image generated by the image generating unit 53, the scan plan modifying unit 56 associates a scan plan with the energy level EL and the energy width EW corresponding to the extended energy bin image (e.g., incorporate the level and width in the scan plan as preset values). As a result, when a next scan is performed according to this scan plan, the image generating unit 53 can be configured to generate an image having the energy level EL and energy width EW preset in the scan plan as an initial image and display the generated image on the display unit 42. The following describes an exemplary operation of the X-ray CT apparatus using photon counting 10 according to the present embodiment.

Figure 7:
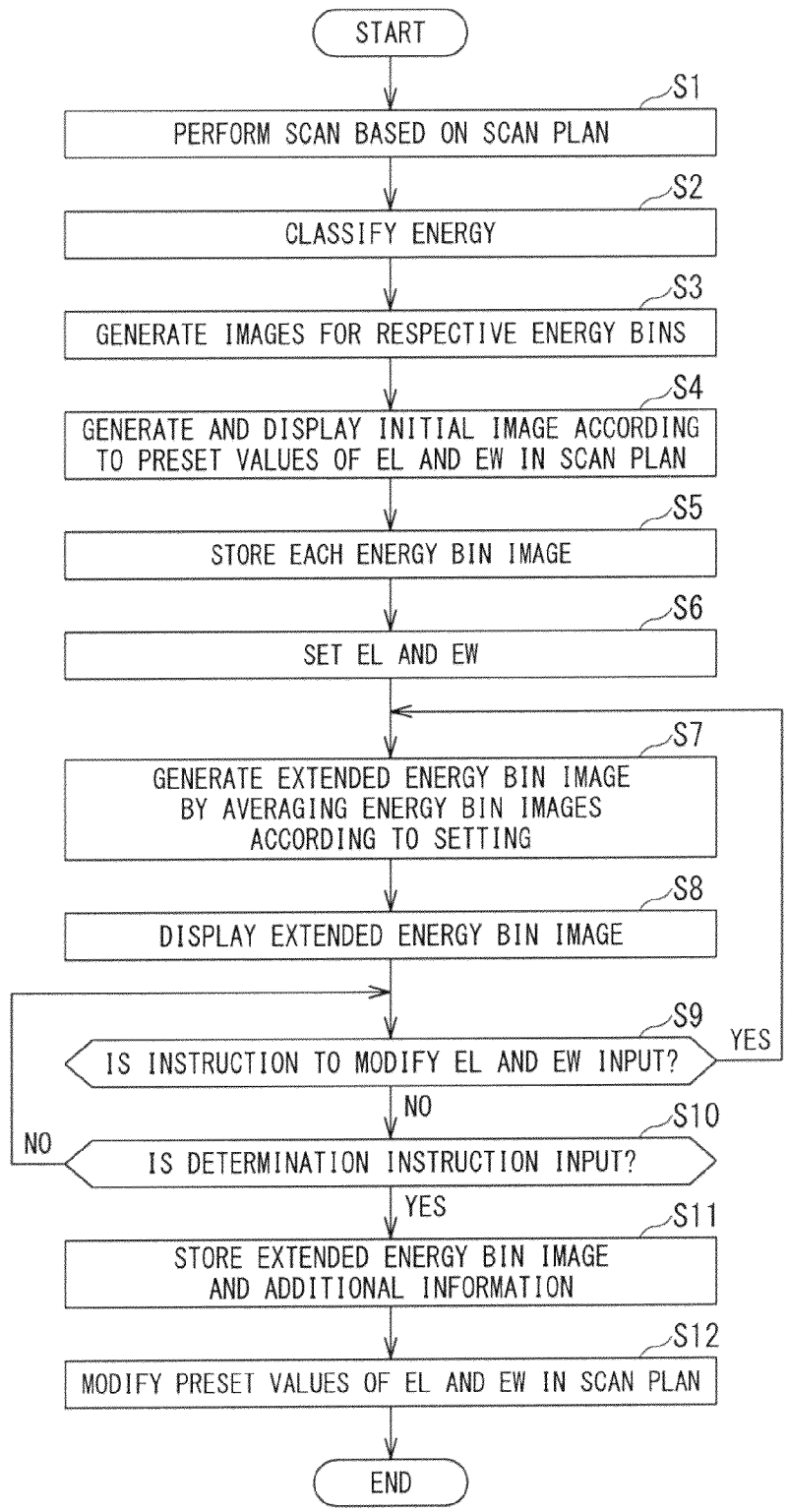
FIG. 7 is a flow chart showing a process executed by the CPU of the main control unit in FIG. 1, for generating an extended energy bin image that has an energy width of multiple energy bins and for modifying the width of the energy bins in response to a user input operation while generating an image according to the modification in real time.

FIG. 7 is a flow chart showing a process executed by the CPU of the main control unit 45 in FIG. 1, for generating an extended energy bin image that has an energy width of multiple energy bins and for modifying the width of the energy bins in response to a user input operation while generating an image according to the modification in real time. Reference numerals each having the prefix "S" in FIG. 7 denote steps in the flow chart. FIG. 7 shows an example in which energy bin images respectively corresponding to a predetermined number of energy bins, including an initial image, are generated and an extended energy bin image is generated by averaging the multiple energy bin images.

First, in step S1, the scan control unit 51 receives an instruction to carry out a scan plan from a user through the inputting unit 41 and controls the scanner apparatus 11 through the controller 32 to perform a scan according to the scan plan.

Next, in step S2, the energy classifying unit 52 controls the DAS 24 through the controller 32 to classify photons passing through the object O into a predetermined number of energy bins depending on the energy of the photons.

Next, in step S3, the image generating unit 53 generates energy bin images respectively corresponding to the predetermined number of energy bins (see FIG. 3).

Next, in step S4, the image generating unit 53 displays one of the predetermined number of generated energy bin images as an initial image on the display unit 42 (see the upper stage of FIG. 4). Alternatively, if an energy level EL and an energy width EW are preset in the scan plan, for example, after the completion of step S11, the image generating unit 53 generates an image having the energy level EL and the energy width EW as an initial image and display the generated initial image on the display unit 42 (see the lower stage of FIG. 4).

Hereinafter, it is assumed that the scan plan includes no preset energy level EL and energy width EW; in addition, the energy bin image corresponding to a predetermined energy bin of a predetermined number of generated energy bin images is displayed on the display unit 42 as an initial image (a representative image of multiple energy bin images).

Next, in step S5, the storage control unit 54 controls the storage unit 44 to store the predetermined number of energy bin images generated by the image generating unit 53. Note that the sequence of steps S4 and S5 may be reversed.

Next, in step S6, the setting unit 55 sets an energy level EL and an energy width EW on the basis of a lesion, a region, a user input, an initial value, an X-ray exposure dose, and other information items.

Next, in step S7, the image generating unit 53 generates an extended energy bin image by assigning weights to and then taking the average of multiple energy bin images that have the energy width EW set by the setting unit 55 and have energy levels around the energy level EL set by the setting unit 55. These multiple energy bin images are some of the energy bin images stored in the storage unit 44.

At this time, the image generating unit 53 superimposes an image (e.g., a character information image) 61 indicating information on the corresponding energy level EL and energy width EW on each of the initial image and the extended energy bin image. The image generating unit 53 may be configured to further add an energy distribution represented by the counts of photons to the extended energy bin image and superimpose the image 62 indicating information on the corresponding energy level EL and the image 63 indicating information on the corresponding energy width EW on the energy distribution.

Next, in step S8, the image generating unit 53 displays the generated extended energy bin image on the display unit 42.

Next, in step S9, the setting unit 55 determines whether an instruction to modify the energy level EL and the energy width EW is input by the user through the inputting unit 41. If such an instruction is input, the setting unit 55 resets the energy level EL and the energy width EW according to the input, and the process returns back to step S7. In contrast, if a predetermined time passes without any instruction or an instruction to end the modification is received, then the process proceeds to step S10.

In step S10, the setting unit 55 determines whether an instruction to determine the extended energy bin image is input by the user through the inputting unit 41. If such an instruction is input, the process proceeds to step S11. In contrast, if a predetermined time passes without any instruction, the process returns back to step S9 for waiting an instruction to modify the energy level EL and the energy width EW again.

Next, in step S11, the storage control unit 54 controls the storage unit 71 of the image server 70 network-connected via the network connection unit 43 to store the extended energy bin image in association with additional information.

Next, in step S12, the scan plan modifying unit 56 associates the scan plan with the energy level EL and the energy width EW corresponding to the extended energy bin image determined by the user (e.g., incorporate the level and width in the scan plan as preset values). As a result, when a next scan is performed according to this scan plan, the image generating unit 53, in step S4, can be configured to generate an image having the energy level EL and energy width EW preset in the scan plan as an initial image and display the generated image on the display unit 42. Note that the sequence of steps S11 and S12 may be reversed.

According to the foregoing process, an extended energy bin image having an energy width of multiple energy bins can be generated and the width of the energy bins can be modified in response to a user input operation while an image according to the modification is generated in real time.

The X-ray CT apparatus using photon counting 10 according to the present embodiment can generate an extended energy bin image having an energy width of multiple energy bins. Thus, the X-ray CT apparatus 10 can readily provide an image having high user visibility.

Furthermore, the width of the energy bins may be modified according to a user input operation and an image altered according to the modification can be generated in real time and displayed on the display unit 42, which is highly convenient to a user. The user can modify the energy level EL and the energy width EW while confirming an extended energy bin image altered in real time according to the modification, so that the user can readily confirm the energy level EL and the energy width EW required to obtain a desired image.

Thus, for example, in the case of a high noise level of an energy bin image corresponding to an energy level desired by a user, the user can increase the energy width with the energy level remaining, leading to the generation and display of an extended energy bin image having a lowered noise level. Alternatively, the extended energy bin image may also be created by averaging multiple energy bin images, instead of a single energy bin image.

The X-ray CT apparatus 10 according to the present embodiment can allow the storage unit 71 in the image server 70 to store the determined extended energy bin image in connection with additional information. Thus, an operator of the interpretation apparatus 80 can readily confirm the extended energy bin image and its additional information through the display unit 81 of the interpretation apparatus 80.

The X-ray CT apparatus 10 according to the present embodiment can associate a scan plan with the energy level EL and energy width EW corresponding to the determined extended energy bin image. The X-ray CT apparatus 10 can further generate an image having the energy level EL and energy width EW associated with the scan plan and display the generated image as an initial image (see step S4 in FIG. 7).

Typically, scan plans and suitable energy levels EL and energy widths EW depend on the region, lesion, or case. The X-ray CT apparatus 10 can associate each of the scan plans with its suitable energy level EL and energy width EW. Thus, a user using a scan plan with which an energy level EL and an energy width EW are associated can obtain an initial image that is natively clear. It should be appreciated that the user can readily adjust the energy level EL and energy width EW of the initial image depending on the body shape and age of an object (see steps S7-S9 in FIG. 7).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
processing circuitry configured to
classify photons passing through an object into a number of energy bins in accordance with energy of the photons;
set an energy level and set an energy width spanning a plurality of energy bins of the number of energy bins;
generate an extended energy bin image based on information on the photons classified into the plurality of energy bins, the image having the set energy level and the set energy width spanning the plurality of energy bins; and
when an instruction setting a new energy level and a new energy width is newly acquired from an input interface, generate a new extended energy bin image based on the information on the photons classified into the plurality of energy bins, the image having the new energy level and the new energy width.

2. The X-ray CT apparatus according to claim 1, wherein the processing circuitry is further configured to generate a number of energy bin images, each corresponding to one of the number of energy bins, display one of the number of energy bin images on a display as an initial image, and average a plurality of energy bin images corresponding to said set energy width, thereby generating the extended energy bin image having the energy level and the energy width set by the setting unit, and displaying the generated extended energy bin image on the display.

3. The X-ray CT apparatus according to claim 1, wherein the processing circuitry is further configured to acquire information on a lesion associated with the object and set the energy width spanning the plurality of energy bins depending on the information on the lesion.

4. The X-ray CT apparatus according to claim 1, wherein the processing circuitry is further configured to acquire information on a region of interest and set the energy width spanning the plurality of energy bins depending on the information on the region of interest.

5. The X-ray CT apparatus according to claim 1, wherein the processing circuitry is further configured to acquire instruction information on the energy width from a user through the input interface and set the energy width depending on the instruction information.

6. The X-ray CT apparatus according to claim 1, wherein the processing circuitry is further configured to set the energy level and the energy width based on information on a predetermined energy level and a predetermined energy width.

7. The X-ray CT apparatus according to claim 1, wherein the processing circuitry is further configured to acquire information on an X-ray exposure dose included in a scan plan and set the energy width spanning the plurality of energy bins depending on the information on the X-ray exposure dose.

8. The X-ray CT apparatus according to claim 1, wherein the processing circuitry is further configured to, when the energy width spanning the plurality of energy bins is set, acquire information on an X-ray exposure dose included in a scan plan and adjust the energy width spanning the plurality of energy bins depending on the information on the X-ray exposure dose.

9. The X-ray CT apparatus according to claim 1, wherein the processing circuitry is further configured to generate the extended energy bin image by averaging information on the photons classified into the plurality of energy bins so as to emphasize photons classified into an energy bin associated with the energy level set by the setting unit.

10. The X-ray CT apparatus according to claim 1, wherein the processing circuitry is further configured to superimpose an image indicating information on the energy level and the energy width spanning the plurality of energy bins corresponding to the extended energy bin image, on the extended energy bin image.

11. The X-ray CT apparatus according to claim 10, wherein the processing circuitry is further configured to display an image of an energy distribution represented by counts of the photons to the extended energy bin image and, on the energy distribution, superimpose an image indicating information on the energy level corresponding to the extended energy bin image and an image indicating information on the energy width spanning the plurality of energy bins.

12. The X-ray CT apparatus according to claim 1, wherein the processing circuitry is further configured to associate a scan plan with the energy level and sets the energy width spanning the plurality of energy bins of the number of energy bins.

13. The X-ray CT apparatus according to claim 12, wherein the processing circuitry is further configured to newly associate the scan plan with the energy level and the energy width spanning the plurality of energy bins corresponding to the generated extended energy bin image.

14. The X-ray CT apparatus according to claim 13, wherein the processing circuitry is further configured to acquire an instruction to determine the extended energy bin image from the user through the input interface, and in response to the instruction, newly associate the scan plan with the energy level and the energy width corresponding to the extended energy bin image.

15. The X-ray CT apparatus according to claim 14, wherein the processing circuitry is further configured to, in response to the instruction, control a memory to store the extended energy bin image in association with additional information including the energy level and the energy width spanning the plurality of energy bins corresponding to the extended energy bin image.

16. The X-ray CT apparatus according claim 12, wherein the processing circuitry is further configured to generate an image having the energy level and the energy width associated with the scan plan as the initial image.

17. The X-ray CT apparatus according to claim 1, wherein the processing circuitry is further configured to set a mean energy of the energy width spanning the plurality of energy bins of the number of energy bins as the energy level.

18. The X-ray CT apparatus according to claim 1, wherein the processing circuitry is further configured to define energy differences between the set energy level and each of middle energies of surrounding energy bins corresponding to the set energy width, assign weights to the surrounding energy bins according to the corresponding defined energy differences, and generate the extended energy bin image by weighted averaging information on photons classified into the surrounding energy bins based on the assigned weights.

19. An X-ray CT apparatus controlling method, comprising:
classifying photons passing through an object into a number of energy bins in accordance with energy of the photons;
setting an energy level and setting an energy width spanning a plurality of energy bins of the number of energy bins;
generating an extended energy bin image based on information on the photons classified into the plurality of energy bins, the image having the set energy level and the set energy width spanning the plurality of energy bins; and
when an instruction setting a new energy level and a new energy width is newly acquired, generating a new extended energy bin image based on the information on the photons classified into the plurality of energy bins, the image having the new energy level and the new energy width.

* * * * *